United States Patent [19]

Lawson et al.

[11] Patent Number: 5,254,702

[45] Date of Patent: Oct. 19, 1993

[54] PROCESS FOR THE PREPARATION OF 2-OXYTETRAHYDROFURANS

[75] Inventors: Ann P. Lawson, Lancashire, Del.; Jeffrey A. Klang, Media, Pa.

[73] Assignee: Arco Chemical Technology, L.P., Wilmington, Del.

[21] Appl. No.: 868,050

[22] Filed: Apr. 13, 1992

[51] Int. Cl.$^5$ ................... C07D 307/20; C07D 307/28
[52] U.S. Cl. ..................................... 549/475; 549/507
[58] Field of Search ................. 549/475, 479, 507

[56] References Cited

U.S. PATENT DOCUMENTS

| | | | |
|---|---|---|---|
| 4,123,444 | 10/1978 | Smith | 260/347 |
| 4,129,579 | 12/1978 | Kang et al. | 549/507 |
| 4,139,542 | 2/1979 | Smith | 260/347.8 |
| 4,529,808 | 7/1985 | Lin et al. | 549/475 |
| 4,533,742 | 8/1985 | Lin et al. | 549/475 |
| 5,008,408 | 4/1991 | Fischer et al. | 549/429 |

FOREIGN PATENT DOCUMENTS 0106860 9/1977 Japan.
58-13580 1/1983 Japan.

OTHER PUBLICATIONS

Japanese Kokai No. 03-192,116 (*Chem. Abstr.* 115 156951h) 1991.
Japanese Kokai No. 02-11,622 (*Chem. Abstr.* 112 236049e) 1989.
Japanese Kokai No. 03-146,509 (*Chem. Abstr.* 115 209876c) 1991.
*Heterocycles* 6 (1977) 529, (*Chem. Abstr.* 87 23202c) 1976.
Japanese Kokai No. 56-015284 (*Chem. Abstr.* 95 7323c) 1981.
Japanese Kokai No. 56-015285 (*Chem. Abstr.* 95 7322b) 1981.
Japanese Kokai No. 52-093778 (Chem. Abstr. 88 121226d) 1977.
Japanese Kokai No. 52-106860 (English Translation) 1977.
European Patent Appln. No. 434,067 (*Chem. Abstr.* 115 233814b) 1991.
*J. Org. Chem.* 57 (1992) 2195-2196.

*Primary Examiner*—C. Warren Ivy
*Assistant Examiner*—A. A. Owens
*Attorney, Agent, or Firm*—Jonathan L. Schuchardt

[57] ABSTRACT

A two-phase process for preparing 2-oxytetrahydrofurans is disclosed. Aqueous 4-hydroxybutanal, which is readily available from a commercial hydroformylation process, is combined with an organic solution of a hydroxy compound in the presence of an acid catalyst to produce a 2-oxytetrahydrofuran. 2-Oxytetrahydrofurans are useful intermediates for pharmaceuticals or for the synthesis of 2,3-dihydrofuran.

16 Claims, No Drawings

PROCESS FOR THE PREPARATION OF 2-OXYTETRAHYDROFURANS

FIELD OF THE INVENTION

The invention relates to the synthesis of 2-oxytetrahydrofurans. In particular, a synthesis of 2-oxytetrahydrofurans from aqueous 4-hydroxybutanal (2-hydroxytetrahydrofuran) is described.

BACKGROUND OF THE INVENTION

2-Oxytetrahydrofurans are useful intermediates for the synthesis of 2,3-dihydrofuran, a monomer that polymerizes to give degradable polymers (see, for example, JP Kokai Nos. 03-192,116 [*Chem. Abstr.* 115 256951h], 02-11,622 [*Chem. Abstr.* 112 236049e], and 03-146,509 [*Chem. Abstr.* 115 209876c], and European Patent Application No. 434,067 [*Chem. Abstr.* 115 233814b]). 2-Oxytetrahydrofurans are also useful in the pharmaceutical area for the synthesis of tetrahydrofuryl-substituted fluorouracils (*Heterocycles* 6 (1977) 529 [*Chem. Abstr.* 87 23202c]; JP Kokai No. 56-015284 [*Chem. Abstr.* 95 7323c]; JP Kokai No. 56-015285 [*Chem. Abstr.* 95 7322b]; JP Kokai No. 52-093778 [*Chem. Abstr.* 88 121226d]).

Synthetic routes to 2-oxytetrahydrofurans are known, but most require expensive reagents or starting materials, give low yields, or involve complicated processes.

Japanese Patent Application Kokai No. 52-106860 describes a single-phase process for producing 2-oxytetrahydrofurans from anhydrous 2-hydroxytetrahydrofuran using an acid catalyst. The reference teaches that 2-hydroxytetrahydrofuran is easily manufactured in two steps from γ-butyrolactone. Unfortunately, γ-butyrolactone and the process to make 2-hydroxytetrahydrofuran from γ-butyrolactone are actually quite expensive.

In aqueous media, 2-hydroxytetrahydrofuran and 4-hydroxybutanal are believed to equilibrate:

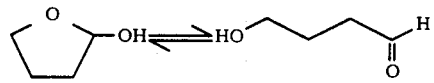

These compounds are structural isomers, and are inseparable for practical purposes.

An inexpensive source of 4-hydroxybutanal is an aqueous stream of the aldehyde that is produced when allyl alcohol is hydroformylated in the presence of a rhodium catalyst. The aqueous 4-hydroxybutanal (about 12% aldehyde) is ordinarily hydrogenated to give commercially important 1,4-butanediol, which can be converted to other important compounds such as tetrahydrofuran, γ-butyrolactone, and N-methyl-2-pyrrolidone.

Equilibrium complicates the synthesis of pure 2-oxytetrahydrofurans from aqueous mixtures of 4-hydroxybutanal and alcohols. When a substantial amount of water is present, the equilibrium lies to the left and favors formation of 2-hydroxytetrahydrofuran rather than the desired 2-oxytetrahydrofuran product:

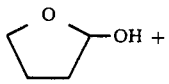

Shifting the equilibrium further to the right by distilling away water is not feasible, and is unacceptable commercially because it is energy intensive. Using an excess amount of the hydroxy compound favors the desired 2-oxytetrahydrofuran, but adds excessive cost, especially if the hydroxy compound is relatively valuable.

An economical process for producing 2-oxytetrahydrofurans is needed. A preferred process would use readily available aqueous 4-hydroxybutanal. A process that overcomes the difficulties of preparing acetals in acidic aqueous media, and permits high conversion of 4-hydroxybutanal and simple isolation of relatively pure 2-oxytetrahydrofurans is especially needed.

SUMMARY OF THE INVENTION

The invention is a process for producing a 2-oxytetrahydrofuran. The process comprises reacting, in the presence of an acid catalyst, a two-phase mixture of: (a) an aqueous solution containing 4-hydroxybutanal, and (b) a solution of a hydroxy compound in a nonpolar organic solvent. Surprisingly, the 4-hydroxybutanal is converted in high yield to a 2-oxytetrahydrofuran, which is recovered selectively in the nonpolar organic solvent. The organic solution is easily separated from the aqueous phase, and the 2-oxytetrahydrofuran is isolated from the organic solvent by any convenient means, such as distillation.

The 2-oxytetrahydrofuran product can be thermally decomposed in the liquid or vapor phase to produce 2,3-dihydrofuran.

DETAILED DESCRIPTION OF THE INVENTION

The process of the invention comprises reacting a two-phase mixture: an aqueous solution of 4-hydroxybutanal, and an organic phase that contains a hydroxy compound.

The aqueous phase contains any desired amount of 4-hydroxybutanal obtained from any source. A suitable aqueous 4-hydroxybutanal solution is conveniently available from a commercial process involving hydroformylation of allyl alcohol. The aqueous stream typically contains about 10–13 wt. % aldehydes, and this solution is suitable for use in the process of the invention without modification. Of course, aqueous solutions of any desired 4-hydroxybutanal concentration can be used since the aldehyde concentration is not especially critical. In aqueous media, 2-hydroxytetrahydrofuran and 4-hydroxybutanal are believed to equilibrate, as described in the background section of the application. These compounds are inseparable for practical purposes, but are equally useful in the process of the present invention.

The organic phase includes a nonpolar organic solvent and a hydroxy compound that is soluble in the organic solvent. The nonpolar organic solvent is substantially water-immiscible, and combination of the organic solvent with aqueous 4-hydroxybutanal results in a two-phase mixture. Suitable nonpolar organic solvents are those in which the 2-oxytetrahydrofuran product is soluble. Suitable solvents include aromatic and aliphatic hydrocarbons, halogenated hydrocarbons, ketones, esters, ethers, and the like, and mixtures thereof. Preferred solvents are aliphatic and aromatic hydrocarbons. Hexane is particularly preferred. Preferred nonpolar organic solvents are those that can be readily separated from the 2-oxytetrahydrofuran product by distillation.

The hydroxy compound is any organic compound that has a free primary, secondary, or tertiary hydroxyl group. Suitable hydroxy compounds include saturated and unsaturated linear, branched, and cyclic aliphatic and aromatic alcohols. Diols, triols, and polyols are suitable. Polyether and polyester polyols such as polypropylene glycols, polytetramethylene ether glycols, and the like are suitable. Glycol ethers such as propylene glycol methyl ether and diethylene glycol ethyl ether are also suitable. Preferred hydroxy compounds are aliphatic alcohols having from 1 to 10 carbons. The hydroxy compound has good solubility in the nonpolar organic solvent used.

The amount of hydroxy compound used is not critical. Preferably, the amount used will be within the range of about 0.1 to about 5 equivalents per equivalent of 4-hydroxybutanal. A larger excess of hydroxy compound can be used if desired. A particularly preferred range for the hydroxy compound is from about 0.8 to about 1.5 equivalents per equivalent of 4-hydroxybutanal.

When less than one equivalent of hydroxy compound per equivalent of 4-hydroxybutanal is used, conversion of the hydroxy compound is typically near quantitative, and any unreacted 4-hydroxybutanal remains in the aqueous phase. When the hydroxy compound is used in excess, 4-hydroxybutanal conversion is near quantitative, with excellent selectivity to the desired 2-oxytetrahydrofuran.

An acid catalyst is used in the process of the invention. The acid can be an organic acid such as acetic acid, trifluoroacetic acid, methanesulfonic acid, p-toluenesulfonic acid, or the like. Soluble inorganic acids such as hydrochloric acid and sulfuric acid are also suitable. Insoluble inorganic acids such as acidic ion-exchange resins, acid-washed clays, zeolites, and the like can be used. Preferred acid catalysts, because they are easily separated from the other components and reused, are the insoluble inorganic acids.

Any desired amount of acid catalyst can be used. As is well understood by those skilled in the art, the amount of catalyst needed will depend on many factors, including the specific reaction conditions used and the type of acid catalyst employed. With organic acids and soluble inorganic acids, a trace amount of catalyst usually suffices. Larger amounts of insoluble inorganic acids are typically used.

The process of the invention is performed by mixing the organic solution containing the hydroxy compound with aqueous 4-hydroxybutanal in the presence of the acid catalyst to give a reaction mixture having two liquid phases. The 2-oxytetrahydrofuran product is continuously extracted into the organic phase as it forms, and can be obtained in excellent yield. When the reaction is complete, the phases can be separated, and the 2-oxytetrahydrofuran can be isolated from the organic phase. Distillation is typically a convenient way to separate the 2-oxytetrahydrofuran from the organic phase, although any suitable means of separation can be employed.

The process of the invention can be performed batchwise, semi-batchwise, or continuously, as desired. A continuous process is preferred.

The process of the invention proceeds smoothly over a broad temperature range, and is most conveniently performed at temperatures within the range of about 20° C. to about 100° C. A more preferred range is from about 20° C. to about 40° C. Reactions will generally be complete within 24 hours at room temperature, and often will be complete in less than one hour.

The following examples merely illustrate the invention. Those skilled in the art will recognize numerous variations that are within the spirit of the invention and scope of the claims.

EXAMPLE 1

Preparation of 2-n-Butoxytetrahydrofuran using "Amberlyst-15" resin

Aqueous 4-hydroxybutanal (502 g of 10.2 wt. % solution, 0.58 mol, 1.0 eq.), n-butanol (34.6 g, 0.47 mol, 0.80 eq.), hexanes (500 mL), and "Amberlyst-15" resin (product of Rohm and Haas Company, 2.3 g) are charged to a 2-L glass reaction vessel equipped with a magnetic stir bar. The two-phase mixture is stirred at ambient temperature (22° C.) for 17 h. The two liquid phases are separated from the ion-exchange resin. The hexane layer, which is separated from the aqueous phase and analyzed by gas chromatography (GC), contains 14.8 wt. % of 2-n-butoxytetrahydrofuran (59.4 g, 88.5% yield). Product identity is confirmed by infrared, $^1H$ NMR, and $^{13}C$ NMR spectroscopies. The aqueous phase contains 4.2% unreacted 4-hydroxybutanal.

EXAMPLE 2

Preparation of 2-n-Butoxytetrahydrofuran using Sulfuric acid

The procedure of Example 1 is followed with 4-hydroxybutanal (252 g of 10.2 wt. % solution, 0.29 mol, 1.0 eq.), n-butanol (17.3 g, 0.23 mol, 0.80 eq.), and hexanes (500 mL). Concentrated sulfuric acid (0.5 mL) is used in place of "Amberlyst-15" resin. After 18 h of stirring at room temperature, the hexane phase contains 8.9% of 2-n-butoxytetrahydrofuran by GC (32.8 g, 98% yield).

EXAMPLE 3

Preparation of 2-Allyloxytetrahydrofuran

The procedure of Example 1 is followed with 4-hydroxybutanal (250 g of 11.0 wt. % solution, 0.31 mol, 1.0 eq.), allyl alcohol (13.8 g, 0.24 mol, 0.80 eq.), and hexanes (500 mL). Concentrated sulfuric acid (0.5 mL) is used in place of the ion-exchange resin. After stirring for 18 h at room temperature the hexane phase contains 5.96% of 2-allyloxytetrahydrofuran (21.3 g, 70% yield). The aqueous phase contains 5.3% of 4-hydroxybutanal and 1.9% of allyl alcohol.

EXAMPLE 4

The procedure of Example 1 is followed with 4-hydroxybutanal (20.0 g of 11.5 wt. % solution, 26 mmol, 1.0 eq.), allyl alcohol (3.26 g, 56 mmol, 2.2 eq.), and hexanes (50 mL). Concentrated hydrochloric acid (2 drops) is used in place of the ion-exchange resin. After 3 h of stirring at room temperature, the hexane phase contains 8.8% of 2-allyloxytetrahydrofuran (3.1 g, 92.5% yield).

EXAMPLES 5-13

Additional 2-oxytetrahydrofurans are prepared according to the process of the invention by following the general procedure of Example 1, but with various alcohols and acid catalysts. All reactions are performed at ambient temperature (20°-23° C.) using 10.0-11.5 wt. % aqueous 4-hydroxybutanal. Overall yields of the 2-oxytetrahydrofurans are 68-98% when the two-phase process of the invention is used (see Table 1). Comparative Examples 7 and 11 show reduced yields of the 2-oxytetrahydrofurans in the absence of the nonpolar solvent. (Compare the results of Example 6 with those of Comparative Example 7, and compare the results of Example 10 with those of Comparative Example 11). Comparative Example 8 shows the importance of using an acid catalyst in the process.

The preceding examples are meant only as illustrations; the true metes and bounds of the invention ar defined by the following claims.

TABLE 1

Preparation of 2-Oxytetrahydrofurans by Two-Phase Reaction of Aqueous 4-Hydroxybutanal with Hydroxy Compounds[a]

| Example # | Hydroxy Compound (equiv.[b]) | Solvent (M[c]) | Acid Catalyst | Time (h) | Yield of 2-OxyTHF (%)[d] |
|---|---|---|---|---|---|
| 5 | n-butanol (0.8) | hexanes (0.5) | "Amberlyst-15" resin | 17 | 94 |
| 6 | n-butanol (2.0) | hexanes (1.0) | $H_2SO_4$ | 3.5 | 98 |
| C7 | n-butanol (2.0) | none | $H_2SO_4$ | 3.5 | 71 |
| C8 | n-butanol (2.5) | hexanes (1.0) | none | 3.5 | 8 |
| 9 | n-butanol (0.5) | hexanes (0.3) | HCl | 3.0 | 98 |
| 10 | ethanol (2.0) | hexanes (1.0) | $H_2SO_4$ | 18 | 77 |
| C11 | ethanol (2.0) | none | $H_2SO_4$ | 18 | 24 |
| 12 | benzyl alcohol (0.8) | hexanes (0.5) | $H_2SO_4$ | 18 | 95 |
| 13 | 2-hexanol (0.8) | hexanes (0.5) | $H_2SO_4$ | 18 | 68 |

[a]All reactions performed at room temperature using 10.0-11.5 wt % aq. 4-hydroxybutanal.
[b]Equivalents of hydroxy compound per equivalent of 4-hydroxybutanal.
[c]Molarity (moles per liter) of hydroxy compound in hexanes.
[d]Yield determined by gas chromatography.

We claim:

1. A process for producing a 2-oxytetrahydrofuran, said process comprising reacting a two-phase mixture of:
   (a) an aqueous solution containing 4-hydroxybutanal, and
   (b) a solution of a hydroxy compound in a nonpolar organic solvent;
in the presence of an acid catalyst to produce a solution of the 2-oxytetrahydrofuran in the nonpolar organic solvent.

2. The process of claim 1 wherein the organic solution containing the 2-oxytetrahydrofuran is separated from the aqueous phase, and the 2-oxytetrahydrofuran is isolated from the organic solution.

3. The process of claim 1 wherein the hydroxy compound is selected from the group consisting of saturated and unsaturated linear, branched, and cyclic aliphatic and aromatic alcohols, including diols, triols, and polyols.

4. The process of claim 1 wherein the nonpolar organic solvent is selected from the group consisting of aliphatic and aromatic hydrocarbons.

5. The process of claim 1 wherein the acid catalyst is an insoluble inorganic acid catalyst.

6. The process of claim 5 wherein the insoluble inorganic acid catalyst is an acidic ion-exchange resin.

7. The process of claim 1 wherein the 2-oxytetrahydrofuran product is thermally decomposed in the liquid or vapor phase to produce 2,3-dihydrofuran.

8. A process for producing a 2-oxytetrahydrofuran, said process comprising:
   (a) reacting a two-phase mixture of:
      (i) an aqueous solution containing 4-hydroxybutanal, and
      (ii) a solution of a hydroxy compound in a nonpolar organic solvent;
      in the presence of an insoluble inorganic acid catalyst to produce a solution of the 2-oxytetrahydrofuran in the nonpolar organic solvent;
   (b) separating the organic phase containing the 2-oxytetrahydrofuran from the aqueous phase; and
   (c) isolating the 2-oxytetrahydrofuran from the organic solution.

9. The process of claim 8 wherein the hydroxy compound is selected from the group consisting of saturated and unsaturated linear, branched, and cyclic aliphatic and aromatic alcohols, including diols, triols, and polyols.

10. The process of claim 8 wherein the nonpolar organic solvent is selected from the group consisting of aliphatic and aromatic hydrocarbons.

11. The process of claim 8 wherein the insoluble inorganic acid catalyst is an acidic ion-exchange resin.

12. The process of claim 8 wherein the 2-oxytetrahydrofuran product is thermally decomposed in the liquid or vapor phase to produce 2,3-dihydrofuran.

13. A process for producing 2,3-dihydrofuran, said process comprising:
   (a) reacting a two-phase mixture of:
      (i) an aqueous solution containing 4-hydroxybutanal, and
      (ii) a solution of a hydroxy compound in a nonpolar organic solvent;
      in the presence of an insoluble inorganic acid catalyst to produce a solution of a 2-oxytetrahydrofuran in the nonpolar organic solvent;
   (b) separating the organic phase containing the 2-oxytetrahydrofuran from the aqueous phase;
   (c) isolating the 2-oxytetrahydrofuran from the organic solution; and
   (d) thermally decomposing the 2-oxytetrahydrofuran in the liquid or vapor phase to produce 2,3-dihydrofuran.

14. The process of claim 13 wherein the hydroxy compound is selected from the group consisting of saturated and unsaturated linear, branched, and cyclic aliphatic and aromatic alcohols, including diols, triols, and polyols.

15. The process of claim 13 wherein the nonpolar organic solvent is selected from the group consisting of aliphatic and aromatic hydrocarbons.

16. The process of claim 13 wherein the insoluble inorganic acid catalyst is an acidic ion-exchange resin.

* * * * *